United States Patent
Eitan et al.

(10) Patent No.: US 11,592,411 B2
(45) Date of Patent: Feb. 28, 2023

(54) PRESERVATIVE DETECTION IN BEVERAGE SYRUP

(71) Applicant: Talking Rain Beverage Company, Inc., Preston, WA (US)

(72) Inventors: Roni Greenberg Eitan, Kenmore, WA (US); Rachel Montenegro, Seattle, WA (US); Vesna Vujic-Kuzmanovic, Seattle, WA (US); Jagriti Sharma, Issaquah, WA (US); Erik Throndsen, Maple Valley, WA (US)

(73) Assignee: Talking Rain Beverage Company, Inc., Preston, WA (US)

( * ) Notice: Subject to any disclaimer, the term of this patent is extended or adjusted under 35 U.S.C. 154(b) by 349 days.

(21) Appl. No.: 17/023,211

(22) Filed: Sep. 16, 2020

(65) Prior Publication Data

US 2022/0082519 A1    Mar. 17, 2022

(51) Int. Cl.
| | |
|---|---|
| *G01N 27/06* | (2006.01) |
| *G01N 31/16* | (2006.01) |
| *G01N 31/22* | (2006.01) |
| *A23L 2/02* | (2006.01) |
| *A23L 2/44* | (2006.01) |
| *G01N 33/14* | (2006.01) |

(52) U.S. Cl.
CPC .............. *G01N 27/06* (2013.01); *A23L 2/02* (2013.01); *A23L 2/44* (2013.01); *G01N 31/16* (2013.01); *G01N 31/221* (2013.01); *G01N 33/143* (2013.01)

(58) Field of Classification Search
CPC ...... G01N 27/06; G01N 31/16; G01N 31/221; G01N 33/143; A23L 2/02; A23L 2/44

USPC .............. 324/71.1, 438–439, 692–693
See application file for complete search history.

(56) References Cited

U.S. PATENT DOCUMENTS

| | | | | |
|---|---|---|---|---|
| 7,998,513 | B1 * | 8/2011 | Khurana | G01N 21/41 426/321 |
| 8,323,571 | B1 * | 12/2012 | Khurana | G01N 21/4133 422/82.01 |
| 8,647,570 | B1 * | 2/2014 | Khurana | G01N 21/41 422/62 |
| 8,647,571 | B1 * | 2/2014 | Khurana | A23L 3/3544 422/62 |
| 8,647,572 | B1 * | 2/2014 | Khurana | A23L 3/3544 422/62 |
| 10,238,131 | B2 * | 3/2019 | Bartlett | A23L 3/34 |

(Continued)

FOREIGN PATENT DOCUMENTS

| | | | | |
|---|---|---|---|---|
| CN | 1380973 A | * | 11/2002 | ........... G01N 27/021 |
| CN | 110208415 A | * | 9/2019 | |

(Continued)

*Primary Examiner* — Jermele M Hollington
*Assistant Examiner* — Sean Curtis
(74) *Attorney, Agent, or Firm* — Seed IP Law Group LLP

(57) ABSTRACT

A method for determining whether a syrup contains a preservative at a needed level is provided. The method includes measuring a conductivity of the syrup, determining whether the measured conductivity is below a predetermined conductivity value determined based on a target syrup according to a syrup recipe, and determining whether the preservative is below the needed level in response to the measured conductivity being below the predetermined conductivity value.

20 Claims, 7 Drawing Sheets

(56) References Cited

U.S. PATENT DOCUMENTS

| | | | |
|---|---|---|---|
| 2004/0033299 A1* | 2/2004 | Simmons | A23L 3/3472 |
| | | | 426/541 |
| 2004/0151618 A1* | 8/2004 | Bendiner | A01N 37/10 |
| | | | 422/7 |
| 2018/0035696 A1* | 2/2018 | Bartlett | A21C 1/1425 |
| 2022/0082519 A1* | 3/2022 | Eitan | G01N 31/22 |

FOREIGN PATENT DOCUMENTS

| | | | | |
|---|---|---|---|---|
| KR | 20200101617 A | * | 8/2020 | G01N 27/06 |
| KR | 102177989 B1 | * | 11/2020 | G01N 27/06 |
| WO | WO-2004034765 A2 | * | 4/2004 | A01N 37/10 |

\* cited by examiner

PRESERVATIVE DETECTION IN BEVERAGE SYRUP

BACKGROUND

Technical Field

The present disclosure relates to methods for verifying whether a beverage syrup is batched correctly to ensure the consistency and quality of the beverage syrup. More particularly, the present disclosure relates to methods for determining whether a beverage syrup contains a preservative at a needed level to adequately prevent microbial spoilage.

Description of the Related Art

Many beverage products include preservatives to prevent the growth of harmful microorganisms (e.g., mold, yeast, and bacteria) and to protect products from spoilage or contamination, thus extending the shelf life of the beverage products. Benzoic acid and its salts such as potassium and sodium benzoates as well as sorbic acids and its salt are commonly used as preservatives in beverage products, such as soft drinks, carbonated drinks, sports drinks, sparkling waters, energy drinks, and the like.

The beverage production process begins by the generation of a finished syrup (i.e., beverage syrup) that contains beverage ingredients including preservative. The proportioning standards of these beverage ingredients are set by syrup recipes. However, in preparing each batch of syrup (prior to diluting with still or carbonated water to make beverages), the proportioning standards of the syrup batch may not conform to the target values set by the syrup recipes. For example, a batch of syrup may not contain preservative at the needed level to retard microbial activity. As a result, the shelf life of the beverage products is compromised. The syrup thus needs to be checked to ensure that each batch of syrup contains an adequate amount of preservative.

Currently, batch approval of syrup for quality control is based on evaluating parameters including titratable acidity, organoleptic properties, pH value and Brix. However, none of these parameters is significantly affected by the absence or low level of preservatives, and thus none of these parameters is a valid indicator for the preservative levels of a beverage.

There are various analytical methods for determination of preservative in the syrup such as high performance liquid chromatography (HPLC), and gas chromatography (GC). HPLC is the most common analytical technique for the detection and quantification of the preservative. An obstacle for verifying whether the syrup has been batched correctly with the needed preservative level is that the current analytical methods are time consuming and require advanced equipment and skilled operating personnel (HPLC, for example). Given the high cost of the analytical equipment and the skill requirements for the operating personnel, most beverage manufacturing facilities do not have the capacity to detect preservatives using conventional analytical methods such as HPLC. There remains a need to develop an easy and quick method for detection of possible low levels of potassium benzoate in syrup because having an adequate amount of chemical preservatives such as potassium benzoate is critical to ensure the shelf life of the beverage products.

BRIEF SUMMARY

Provided herein are methods capable of determining partial or complete absence of a preservative in a beverage syrup.

In some embodiments, a method for determining whether a syrup contains a preservative at a needed level includes measuring the conductivity of the syrup, determining whether the measured conductivity is below a predetermined conductivity value determined based on a target syrup according to a syrup recipe, and determining whether the preservative is below the needed level in response to the measured conductivity being below the predetermined conductivity value. In some embodiments, the predetermined conductivity value corresponds to a conductivity value of a syrup containing the preservative in an amount that is at least 80% of the preservative in the target syrup. In some embodiments, determining whether the preservative is below the needed level comprises measuring a pH of the syrup. In some embodiments, determining whether the preservative is below the needed level further comprises determining whether the measured pH is below a predetermined pH value. In some embodiments, the predetermined pH value corresponds to a pH value of the target syrup. In some embodiments, determining whether the preservative is below the needed level further comprises measuring a titratable acidity of the syrup. In some embodiments, determining whether the preservative is below the needed level further comprises determining whether the measured titratable acidity is below a predetermined titratable acidity value. In some embodiments, the predetermined titratable acidity value corresponds a titratable acidity value of the target syrup. In some embodiments, the preservative comprises benzoic acid, potassium benzoate, sodium benzoate, calcium benzoate, potassium sorbate, sodium diacetate, sodium propionate, calcium propionate, methyl paraben, natamycin, or sodium nitrate. In some embodiments, the syrup further comprises an acid and a juice. In some embodiments, the acid comprises citric acid, malic acid, tartaric acid or lactic acid. In some embodiments, the juice comprises one or more fruit juices, one or more vegetable juices, or combinations thereof. In some embodiments, the syrup further comprises a colorant, a sweetener, a vitamin, a mineral, a flavoring agent or combinations thereof.

In some embodiments, a method for determining whether a syrup contains a preservative at a needed level includes measuring a conductivity of the syrup, determining a predetermined conductivity value using a target syrup according to a syrup recipe, determining whether the measured conductivity is below the predetermined conductivity value, measuring a pH and titratable acidity of the syrup in response to the measured conductivity being below the predetermined conductivity value, comparing the measured pH with a predetermined pH value, comparing the measured titratable acidity with a predetermined titratable acidity value, and determining that the syrup does not contain the preservative at the needed level in response to the pH being below the predetermined pH value and the titratable acidity being comparable to the predetermined titratable acidity value. In some embodiments, the predetermined conductivity value corresponds to a conductivity value of a syrup containing the preservative in an amount that is at least 80% of the preservative in the target syrup. In some embodiments, the predetermined pH value corresponds to a pH value of the target syrup. In some embodiments, the predetermined titratable acidity value corresponds to a titratable acidity value of the target syrup. In some embodiments, the syrup further includes an acid and a juice. In some embodiments, the method further includes determining that the syrup contains the acid in an amount below a target amount as set in the syrup recipe in response to the pH being above the predetermined pH value and the titratable acidity being below the predetermined titratable acidity value. In some embodiments, the method further includes determining that the syrup contains the juice in an amount below a target amount as set in a syrup recipe in response to the pH being comparable to the predetermined pH value and the titratable acidity being comparable to the predetermined titratable acidity value.

DETAILED DESCRIPTION

Embodiments of the present disclosure provide a method for determining whether a syrup contains a preservative at a needed level to effectively prevent microbial spoilage of the syrup and finished beverage product. Adequate amount of preservative helps to protect the shelf life of the syrup and finished beverage product. Adequate amount of the preservative can vary depending on the type of syrup being preserved and the length of time the preservation is desired. Given that the conductivity of a syrup is mainly affected by the preservative, acid, and juice in the syrup, and the preservative, acid, and juice affect the pH and titratable acidity of the syrup differently, the method of the present disclosure determines whether an adequate amount of a preservative is present in a syrup by analyzing results from conductivity, pH and titratable acidity measurements of the syrup. As used herein, conductivity refers to electrical conductivity, which may be measured using conventional devices and techniques for measuring electrical conductivity. The method can be carried out without the need of any complicated and expensive equipment. The method of the present disclosure allows monitoring the batch quality of the syrup in a cost effective manner.

Figure 1:
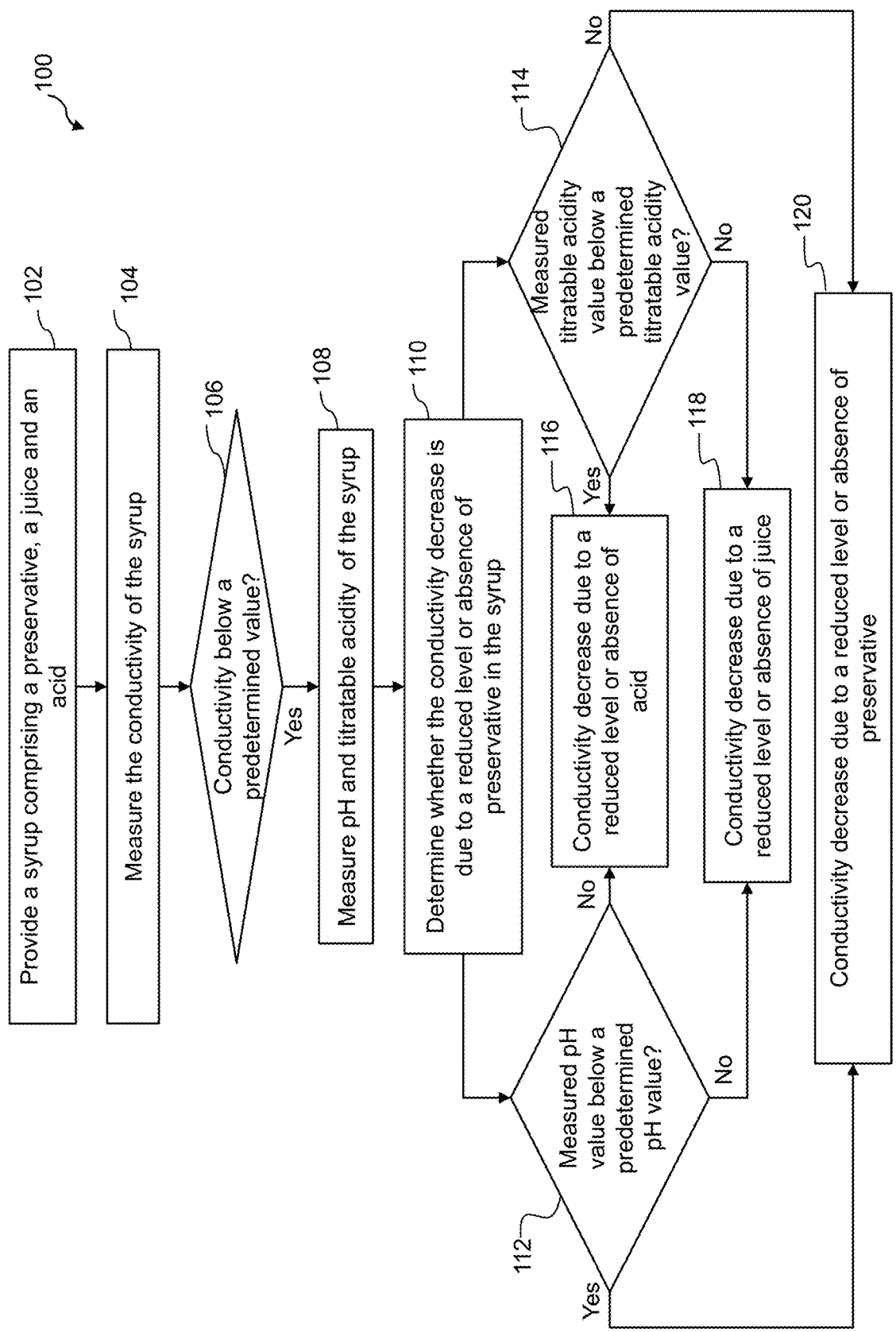
FIG. 1 is a flowchart of a method for determining whether a syrup contains a preservative at a needed level to prevent the syrup against microbiological spoilage, in accordance with some embodiments.

FIG. 1 is a flowchart of a method 100 for determining whether a syrup contains a preservative at a needed level to effectively protect the syrup against microbiological spoilage, in accordance with some embodiments. In some embodiments, additional processes are performed before, during, and/or after the method 100 in FIG. 1, and some processes described herein are replaced or eliminated in some embodiments.

The method 100 includes operation 102, in which a syrup is provided. In some embodiments, the syrup is a beverage syrup from which beverage products are produced. The syrup is in a concentrated form that can be diluted to form the beverage products. In some embodiments, the syrup comprises a preservative, an acid, and a juice. In some embodiments, the syrup can comprise other optional beverage ingredients, including colorants, sweeteners, vitamins, minerals, and flavoring agents. In accordance with some embodiments of the present disclosure, other fluids that include a preservative, an acid and other components that affect the conductivity, and the preservative, acid and other components affect the pH and titratable acidity differently can be evaluated in accordance with methods of the present disclosure to determine whether an adequate amount of a preservative is present in the fluid by analyzing results from conductivity, pH and titratable acidity measurements of the fluid.

The preservative is usable to reduce or eliminate the growth of spoilage-causing microorganisms such as bacteria, molds, fungi, and yeast. Examples of preservatives that can be used in the syrup include, but are not limited to, benzoic acid, potassium benzoate, sodium benzoate, calcium benzoate, potassium sorbate, sodium diacetate, sodium propionate, calcium propionate, methyl paraben, natamycin, sodium nitrate, lactic acid, acetic acid, ascorbic acid, citric acid, malic acid, and mixtures thereof. In some embodiments, the syrup comprises potassium benzoate. The preservative may be present in the syrup in an amount of about 5%, about 4%, about 3%, about 2%, about 1%, about 0.5%, about 0.2%, or about 0.1% by weight. In some embodiments, the syrup contains about 0.12% to about 0.5% (i.e., about 1200 ppm to about 5000 ppm) of preservative by weight. "About," as used herein, denotes that the actual value may be somewhat more or somewhat less than the stated value or range, to within ±20% of the stated value. In other embodiments, about means that the actual value is within ±15% of the stated value. In other embodiments, about means that the actual value is within ±10% of the stated value. In other embodiments, about means that the actual value is within ±5% of the stated value. In other embodiments, about means that the actual value is within ±1% of the stated value.

The acid is usable to control the acidity of the syrup. In some instances, the acid is also usable to provide some preservative properties and/or to stabilize the syrup. In some embodiment, the pH of the syrup is adjusted to pH of about 2.5 to about 4 with a suitable acid. In some embodiments, the acid also functions as a catalyst to activate the preserving properties of a preservative such as potassium benzoate or sodium benzoate. Examples of acids that can be used in the syrup include, but are not limited to, acetic acid, adipic acid, ascorbic acid, butyric acid, citric acid, formic acid, fumaric acid, glyconic acid, lactic acid, malic acid, phosphoric acid, oxalic acid, succinic acid, tartaric acid, and mixtures thereof. In some embodiments, citric acid or malic acid is used in the syrup. The acid may be present in the syrup in an amount of about 5%, about 4%, about 3%, about 2%, about 1%, about 0.5%, about 0.2%, or about 0.1% by weight.

The juice usable in the syrup may be a fruit juice, a vegetable juice, or a blend of juices. Examples of fruit juice include, but are not limited to, orange juice, apple juice, grape juice, pear juice, cranberry juice, raspberry juice, strawberry juice, blueberry juice, blackberry juice, gooseberry juice, elderberry juice, cherry juice, currant juice, pineapple juice, lemon juice, lime juice, grapefruit juice, quince juice, plum juice, prickly pear juice, tangelo juice, pomelo juice, calamondin juice, mango juice, banana juice, kiwi juice, peach juice, nectarine juice, apricot juice, tangerine juice, clementine juice, minneolas juice, satsuma juice, mandarin orange juice, kumquat juice, pomegranate juice, watermelon juice, honeydew melon juice, cantaloupe melon juice, guava juice, papaya juice, passion fruit juice, star fruit juice, tamarind juice, and cupuaca juice. Examples of vegetable juices include, but are not limited to, tomato juice, carrot juice, pepper juice, cabbage juice, broccoli juice, potato juice, celery juice, cucumber juice, cilantro juice, beet juice, wheat grass juice, asparagus juice, zucchini juice, squash juice, rhubarb juice, turnips juice, rutabagas juice, parsnips juice, radish juice, watercress juice, endive juice, escarole juice, lettuce juice, spinach juice, and ginger juice. In some embodiments, the juice is made from orange juice, mango juice, blackberry juice, raspberry juice, and mixtures thereof. In some embodiments, the juice is a juice concentrate. The juice may be present in the syrup in an amount ranging from about 0.1% to about 5%, from about 0.5% to about 4%, or from about 1% to about 3% by weight. In some embodiments, a concentration of the juice in the syrup is about 5%, about 4.5%, about 4%, about 3.5%, about 3%, about 2%, about 2.5%, about 2%, about 1.5%, about 1%, about 0.5%, about 0.2%, or about 0.1% by weight.

The colorant, when included, can provide the syrup with a more aesthetic and/or distinctive appearance. In some embodiments, the colorant includes a natural colorant such as turmeric, saffron, paprika oleoresin, beta carotene, or green chlorophyll obtained from a natural source such as fruit or vegetable. In some other embodiments, the colorant includes an artificial colorant designated in a food additive list such as edible colorant Blue No. 1, edible colorant Green No. 3, edible colorant Red No. 1, edible colorant Red No. 3, or edible colorant Yellow No. 5, edible colorant Yellow No. 6, or a combination thereof. The colorant may be present in the syrup in an amount from about 0.001% to about 1% by weight, from about 0.001% to about 0.5% by weight, and from about 0.0075% to about 0.25% by weight.

The syrup of the present disclosure can contain an effective amount of one or more sweeteners, including carbohydrate sweeteners and natural and/or artificial no/low calorie sweeteners. The amount of the sweetener used (i.e., "effective amount") in the syrup depends upon the particular sweetener used and the sweetness intensity desired. For no/low calorie sweeteners, the amount of the sweeteners varies depending upon the sweetness intensity of the particular sweetener.

The carbohydrate sweeteners include mono- and/or disaccharide sugars. Examples of sugar sweeteners usable in the syrup include, but are not limited to, sucrose, fructose, glucose, and mixtures thereof. Examples of no/low calorie sweeteners include, but are not limited to, aspartame, saccharin, cyclamates, sucralose, acesulfame potassium, stevia or stevia extract, and mixtures thereof.

In some embodiments, the syrup can also be fortified with vitamins and minerals, provided that such vitamins and minerals do not substantially alter the desired properties of the syrup (e.g., ambient display times), and that such vitamins and minerals are chemically and physically compatible with the other essential components of the syrup. Examples of vitamins include, but are not limited to, vitamin A (e.g., vitamin A palmitate), provitamins thereof (e.g., β-carotene), vitamin B1 (e.g., thiamin HCl) and vitamin C (i.e., ascorbic acid), and mixtures thereof. Examples of minerals that can be included in syrups of the present disclosure include, but are not limited to, calcium, magnesium, zinc, iodine, and copper. Any soluble salt of these minerals suitable for inclusion in edible products can be used, for example, calcium carbonate, calcium citrate, calcium malate, calcium-citrate-malate, calcium gluconate, magnesium citrate, magnesium gluconate, magnesium sulfate, zinc chloride, zinc sulfate, potassium iodide, and copper sulfate.

In some embodiments, the syrup can also contain a flavoring agent. The flavoring agent may include an ether, an ester, a ketone, a fatty acid, a phenol, an aromatic alcohol, or a combination thereof. For example, the flavoring agent may include geranyl formate, citronellyl formate, isoamyl formate, cinnamic acid, or a combination thereof.

After providing the syrup, the method 100 proceeds to operation 104, in which the conductivity of the syrup is measured. In some embodiments, the conductivity is measured using a conductivity meter.

After performing the conductivity measurement, the method 100 proceeds to operation 106, in which the conductivity value obtained in operation 104 is compared with a predetermined conductivity value. The predetermined conductivity value is set based on a conductivity value of a syrup containing preservative, acid and juice in exact amounts as set in a syrup recipe. In some embodiments, the predetermined conductivity value is determined as a percentage of the conductivity value of the target syrup chosen by the tester. In some embodiments, to determine the absence of the preservative, the predetermined conductivity value can be selected from a value which amounts to a conductivity of a syrup containing preservative in any amount that is less than the amount of the preservative in a syrup recipe, and if the measured conductivity value falls below the predetermined conductivity value, then it is immediately certain that one or more ingredients might be missing in the syrup and further testing is needed. For example, in some embodiments, the predetermined conductivity value corresponds to the conductivity of a syrup containing preservative in an amount that is about 80% of the amount of preservative set in a syrup recipe. In some other embodiments, the predetermined conductivity value corresponds to the conductivity of a syrup containing preservative in an amount that is about 90% of the amount of preservative set in a syrup recipe. In still some other embodiments, the predetermined conductivity value corresponds to the conductivity of a syrup containing preservative in an amount that is about 95% of the amount of preservative set in a syrup recipe. If the measured conductivity value is less than the predetermined conductivity value, the decrease in conductivity may be due to a less preservative content in the syrup. However, as the syrup also contains acid and juice, less acid content and/or less juice content in the syrup can also cause the conductivity decrease. In order to rule out the possibility that the conductivity decrease is related to the partial or complete absence of acid and/or juice in the syrup, the pH and the titratable acidity of the syrup need to be measured.

Once the measured conductivity value less than the predetermined conductivity value is observed, the method proceeds to operation 108, in which pH and the titratable acidity of the syrup are measured. To measure the pH and titratable acidity of the syrup, the syrup is diluted with water. In some embodiments, the amount of the water in the diluted syrup is based on the finished good (i.e., beverage) dilution. In some embodiments, the syrup is diluted with deionized water.

The pH of the diluted syrup is a measure of the strength and concentration of the dissociated acids present in the diluted syrup. The pH is calculated using the concentration of hydrogen ions in the formula $pH=-\log[H^+]$. The pH of the diluted syrup can be measured by a pH meter, a potentiometric meter, or a colorimetric meter.

The titratable acidity measures the total acidity and indicates the total number of acid molecules (both protonated and unprotonated) in the diluted syrup. The titratable acidity of the diluted syrup is measured potentiometrically with a standardized sodium hydroxide solution of a known concentration.

After performing the pH and titratable acidity measurements, the method proceeds to operation 110, in which whether the conductivity decrease is caused by a reduced level or absence of the preservative in the syrup is determined. The pH value of the diluted syrup is compared with a predetermined pH value, and the titratable acidity value is compared with a predetermined titratable acidity value. The predetermined pH value and the predetermined titratable acidity value correspond to respective pH value and titratable acidity value of a diluted syrup containing the preservative, acid and juice in amounts as set in a syrup recipe.

In operation 110, if the measured titratable acidity value is less than the predetermined titratable acidity value, while the measured pH value is greater than the predetermined pH value or comparable to the predetermined pH value, that is, the difference between the measured pH value and the predetermined pH value is within the measurement error range and/or the expected production variability, then it can be concluded that the conductivity decrease is caused by a reduced level or absence of the acid in the syrup. If the measured titratable acidity is comparable to the predetermined titratable acidity, that is, the difference between the measured titratable acidity and the predetermined titratable acidity is within the measurement error range and/or the expected production variability, and the measured pH value is also comparable to the predetermined pH value, then it can be concluded that the conductivity decrease is caused by the reduced or absence of juice in the syrup. If the measured pH value is less than the predetermined pH value, while the measured titratable acidity value is comparable to the predetermined titratable acidity value, then it can be concluded the conducted decrease is caused by the reduced or absence of preservative in the syrup.

Examples have been set forth below for the purpose of illustration and to describe certain specific embodiments of the disclosure. However, the scope of this disclosure is not to be in any way limited by the examples set forth herein.

EXAMPLES

Example 1

Syrup #1

Materials and Methods

Samples of a first exemplary syrup (also referred to as syrup #1) that contain different levels of potassium benzoate preservative, citric acid, and juice concentrate were prepared. The conductivity, pH and titratable acidity of these syrup #1 samples were measured and analyzed to evaluate the effectiveness of the present method.

Conductivity measurements were performed using a conductivity meter directly on syrup #1 samples. For pH and titratable acidity measurements, each syrup #1 sample was diluted 5 times with water. The pH measurements were performed on the syrup #1 samples using a pH meter. The titratable acidity measurements were performed by titrating 1 N sodium hydroxide (NaOH) with 50 ml of the diluted syrup samples until neutral pH of 7.0 was achieved. The measurement for each sample was repeated at least three times and the measured results were averaged.

Figure 2:
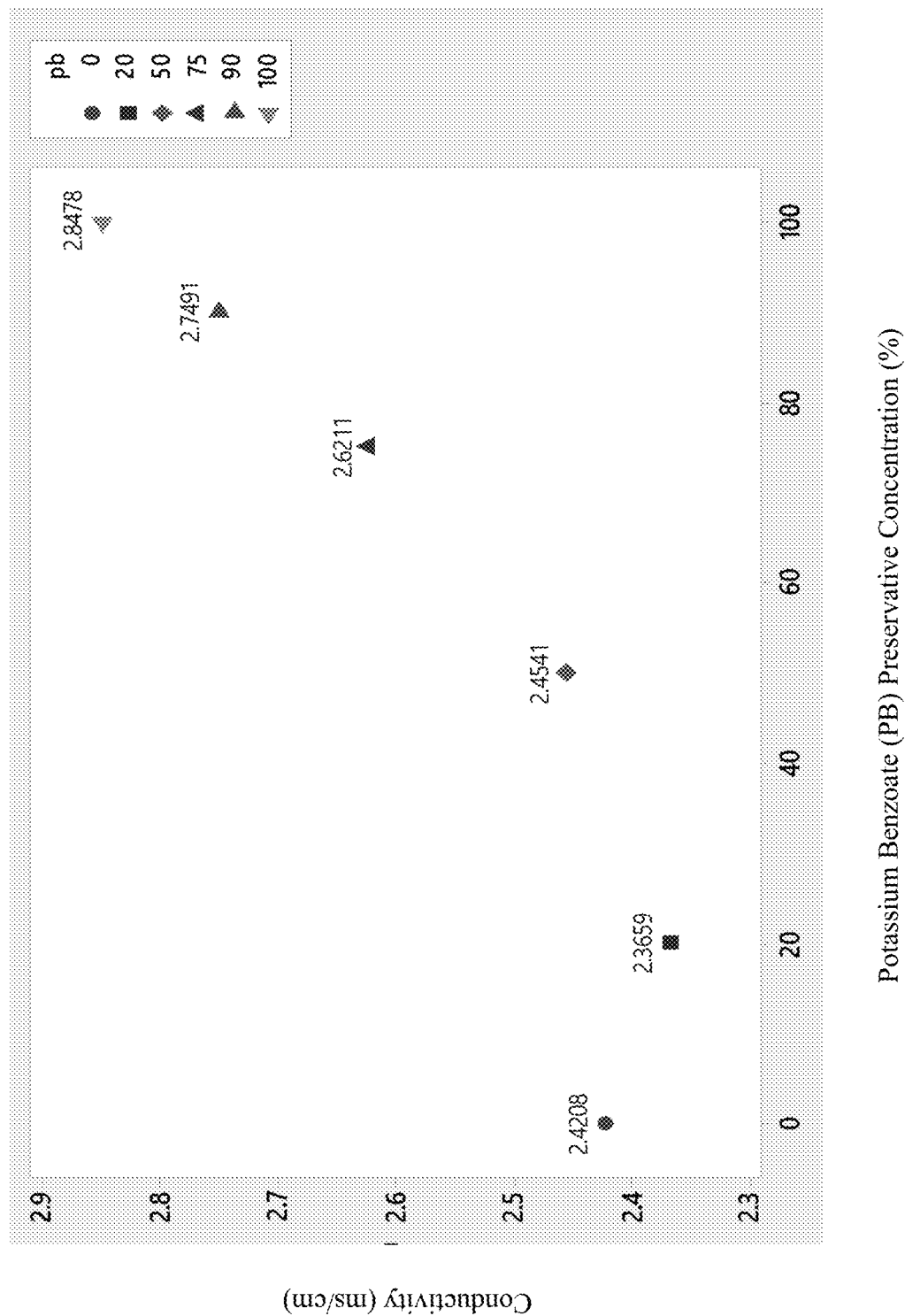
FIG. 2 is a graph of conductivity of a first exemplary syrup as a function of potassium benzoate preservative level.

The effect of preservative concentration on the syrup conductivity was investigated by maintaining the acid and juice concentrations constant and varying the preservative concentration. The measured syrup conductivity as a function of preservative concentration is shown in FIG. 2. As can be seen from FIG. 2, the conductivity of the syrup decreases as the preservative concentration decreases.

Figure 3:
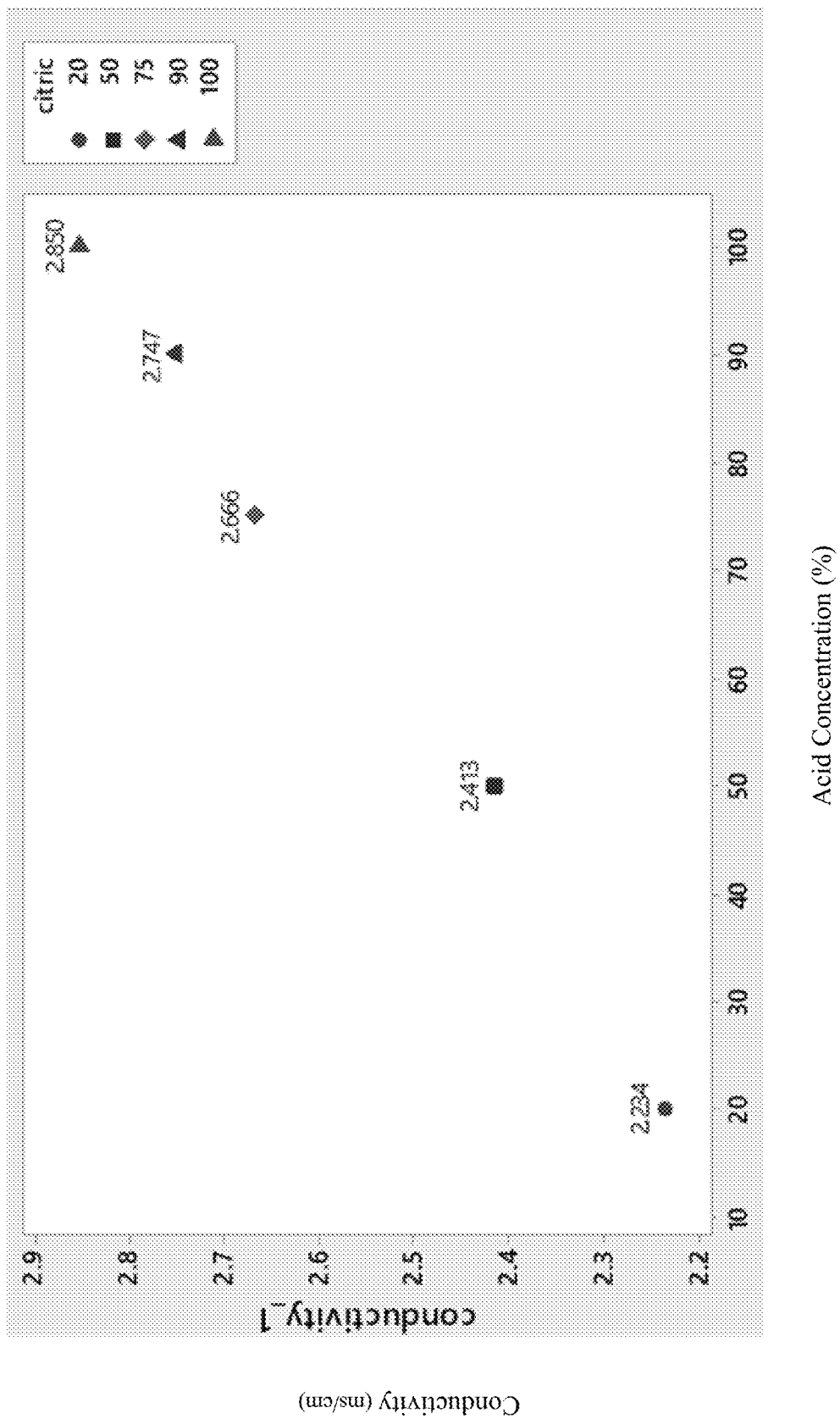
FIG. 3 is a graph of conductivity of the first exemplary syrup as a function of acid level.

The effect of acid concentration on the syrup conductivity was investigated by maintaining the preservative and juice concentrations constant and varying the acid concentration. The measured syrup conductivity as a function of acid concentration is shown in FIG. 3. As can be seen from FIG. 3, the conductivity of the syrup decreases as the acid concentration decreases.

Figure 4:
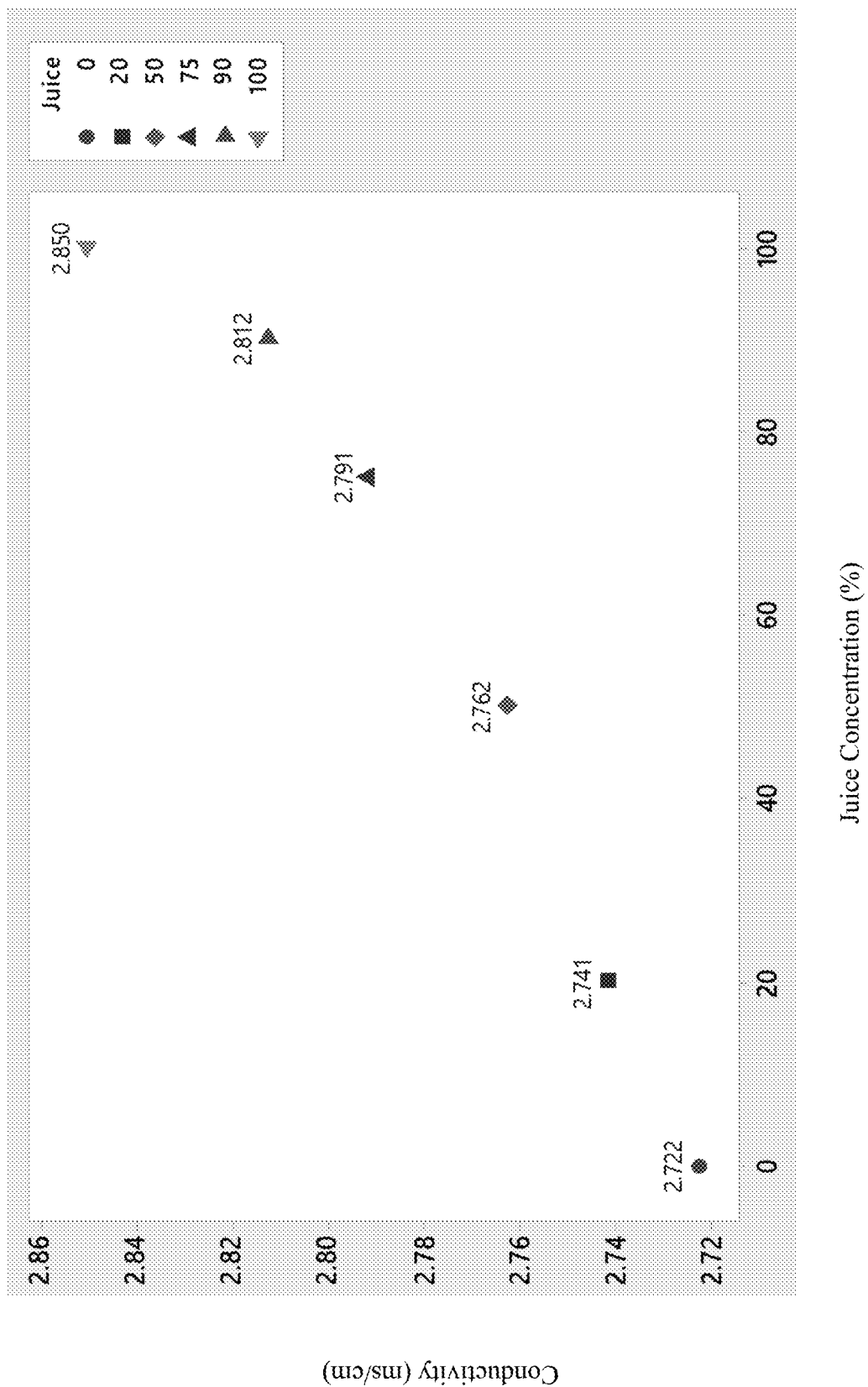
FIG. 4 is a graph of conductivity of the first exemplary syrup as a function of juice level.

The effect of juice concentration on the syrup conductivity was investigated by maintaining the preservative and acid concentrations constant and varying the juice concentration. The measured syrup conductivity as a function of juice concentration is shown in FIG. 4. As can be seen from FIG. 4, the conductivity of the syrup decreases as the juice concentration decreases.

The results in FIGS. 2-4 indicate that if the conductivity of the syrup is decreased, one or more ingredients such as preservative, acid and juice are partially or completely absent in the syrup.

To rule out the possibility that the conductivity decrease is due to the partial or complete absence of acid and/or juice, the titratable acidity and pH of syrup #1 samples were measured. Results are given in the following tables.

Titratable acidity and pH values of syrup #1 samples at different potassium benzoate (PB) preservative levels ranging from 0% (i.e., no PB) to 100% (i.e., target PB level) are summarized in Table 1. As can be seen from Table 1, reducing the potassium benzoate preservative content in the syrup results in a decrease in the pH value, however, the titratable acidity remains about the same (i.e., value variation is within the measurement error range and/or the expected production variability).

TABLE 1

Titratable Acidity and pH Values of Syrup #1
Samples at Different Potassium Benzoate (PB) Levels

| | Potassium Benzoate Levels in Syrup (from 0% to 100% of target PB level) | | | | | |
|---|---|---|---|---|---|---|
| | 0% | 20% | 50% | 75% | 90% | 100% |
| Titratable Acidity | 0.258 | 0.257 | 0.260 | 0.259 | 0.256 | 0.257 |
| pH | 2.60 | 2.60 | 2.68 | 2.75 | 2.77 | 2.83 |

Titratable acidity and pH values of syrup #1 samples at different acid levels ranging from 20% to 100% (i.e., target acid level) are summarized in Table 2. As can be seen from Table 2, reducing the acid content in the syrup results in an increase in the pH value, but a decrease in the titratable acidity.

TABLE 2

Conductivity, Titratable Acidity and pH Values
of Syrup #1 Samples at Different Acid levels

| | Acid Levels in Syrup (from 20% to 100% of target acid level) | | | | |
|---|---|---|---|---|---|
| | 20% | 50% | 75% | 90% | 100% |
| Conductivity [ms/cm] | 2.234 | 2.413 | 2.666 | 2.747 | 2.850 |
| Titratable Acidity | 0.070 | 0.145 | 0.215 | 0.236 | 0.257 |
| pH | 4.1 | 3.39 | 2.78 | 2.75 | 2.83 |

Titratable acidity and pH values of syrup #1 samples at different juice levels ranging from 0% (no juice) to 100% (i.e., target juice level) are summarized in Table 3. As can be seen from Table 3, reducing the juice content in the syrup does not affect pH and titratable acidity of the syrup. The pH and titratable acidity remain about the same (i.e., value variation is within the measurement error range and/or the expected production variability).

TABLE 3

Conductivity, Titratable Acidity and pH Values of Syrup #1 Samples at Different Juice Levels ranging from 0%

| | Juice Levels in Syrup (from 0% to 100% of target juice level) | | | | | |
|---|---|---|---|---|---|---|
| | 0% | 20% | 50% | 75% | 90% | 100% |
| Conductivity [ms/cm] | 2.718 | 2.741 | 2.762 | 2.791 | 2.812 | 2.850 |
| Titratable Acidity | 0.256 | 0.256 | 0.257 | 0.258 | 0.256 | 0.257 |
| pH | 2.92 | 2.92 | 2.94 | 2.94 | 2.97 | 2.83 |

For syrup #1, if the conductivity of the syrup is lower than 2.7 ms/cm, which corresponds to the conductivity of a syrup containing at least 80% of preservative, one or more ingredients, e.g., potassium benzoate preservative, critic acid, and/or juice are partially or completely absent in the syrup. In combination with the conductivity measurement, if the titratable acidity is lower than the titratable acidity target value and the pH is above the pH target value, it can be concluded that the syrup contains less acid. If the titratable acidity and pH are not affected, it can be concluded that the syrup contains less juice. If the pH is lower than the target pH value, but the titratable acidity is not affected, it can be concluded that the syrup contains less potassium benzoate preservative because potassium benzoate affects the pH but does not impact titratable acidity of the syrup.

Example 2

Syrup #2

Materials and Methods

Samples of a second exemplary syrup (also referred to as syrup #2) that contain different levels of potassium benzoate preservative, malic acid, and juice were prepared. The conductivity, pH and titratable acidity of these syrup #2 samples were measured and analyzed to evaluate the effectiveness of the present detection method.

Conductivity measurements were performed using a conductivity meter directly on the syrup #2 samples. For pH and titratable acidity measurements, each syrup #2 sample was diluted 5 times with water. The pH measurements were performed on the syrup #2 samples using a pH meter. The titratable acidity measurements were performed by titrating 1 N sodium hydroxide (NaOH) with 50 ml of the diluted syrup samples until neutral pH of 7.0 was achieved. The measurement for each sample was repeated at least three times and the measured results were averaged.

Figure 5:
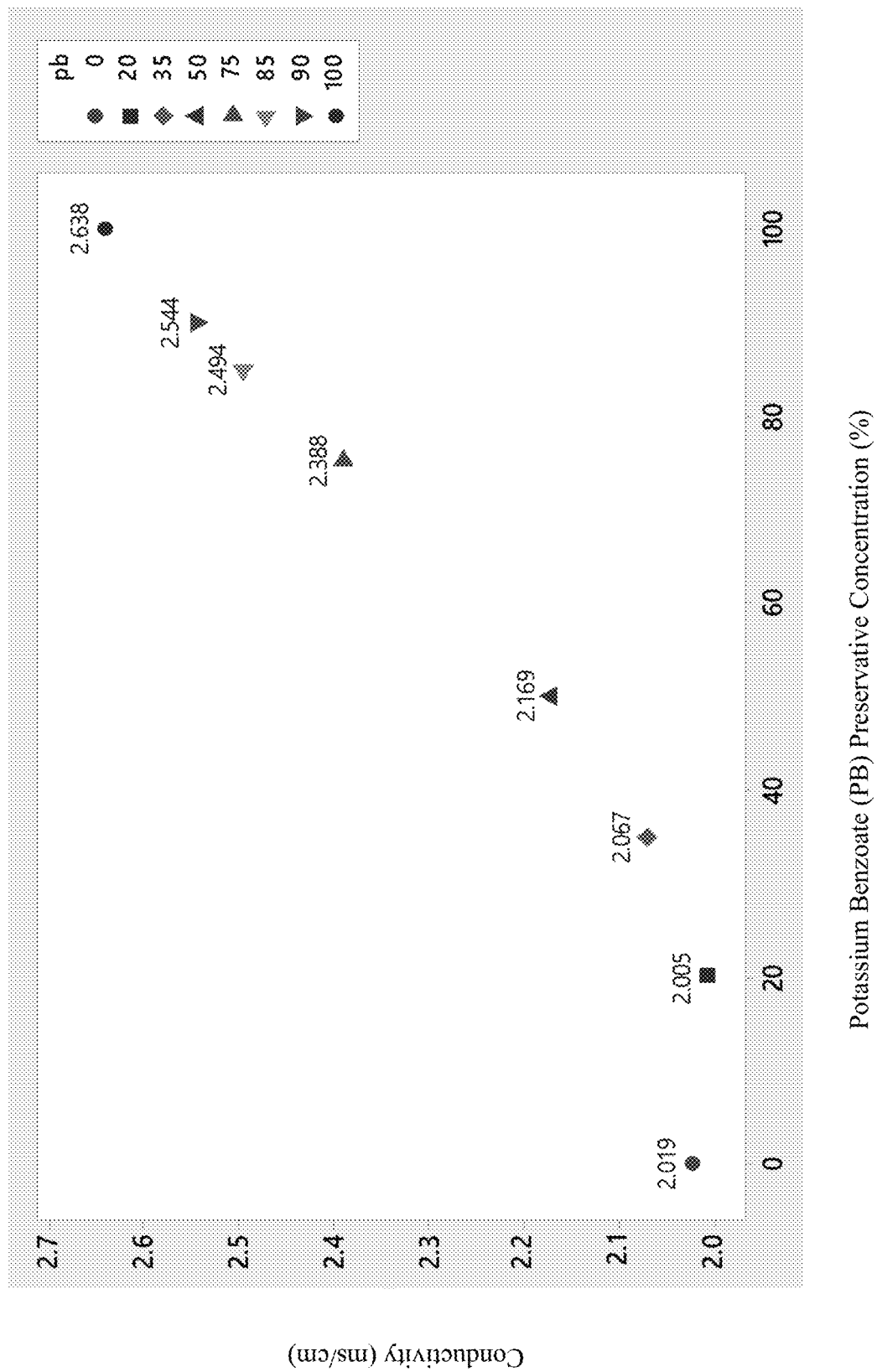
FIG. 5 is a graph of conductivity of a second exemplary syrup as a function of potassium benzoate preservative level.

The effect of preservative concentration on the syrup conductivity was investigated by maintaining the acid and juice concentrations constant and varying the preservative concentration. The measured syrup conductivity as a function of preservative concentration is shown in FIG. 5. As can be seen from FIG. 5, the conductivity of the syrup decreases as the preservative concentration decreases.

Figure 6:
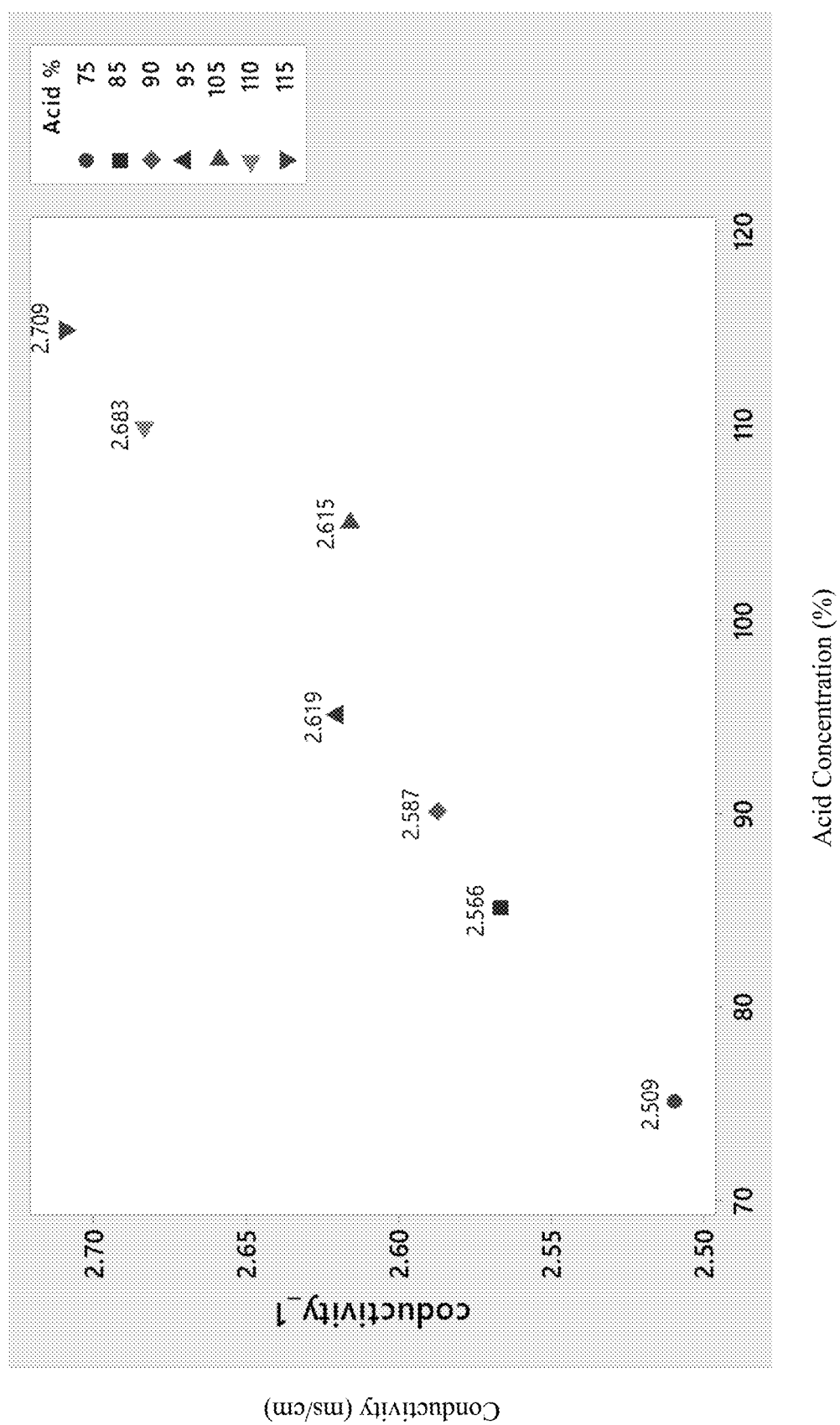
FIG. 6 is a graph of conductivity of the second exemplary syrup as a function of acid level.

The effect of acid concentration on the syrup conductivity was investigated by maintaining the preservative and juice concentrations constant and varying the acid concentration. The measured syrup conductivity as a function of acid concentration is shown in FIG. 6. As can be seen from FIG. 6, the conductivity of the syrup decreases as the acid concentration decreases.

Figure 7:
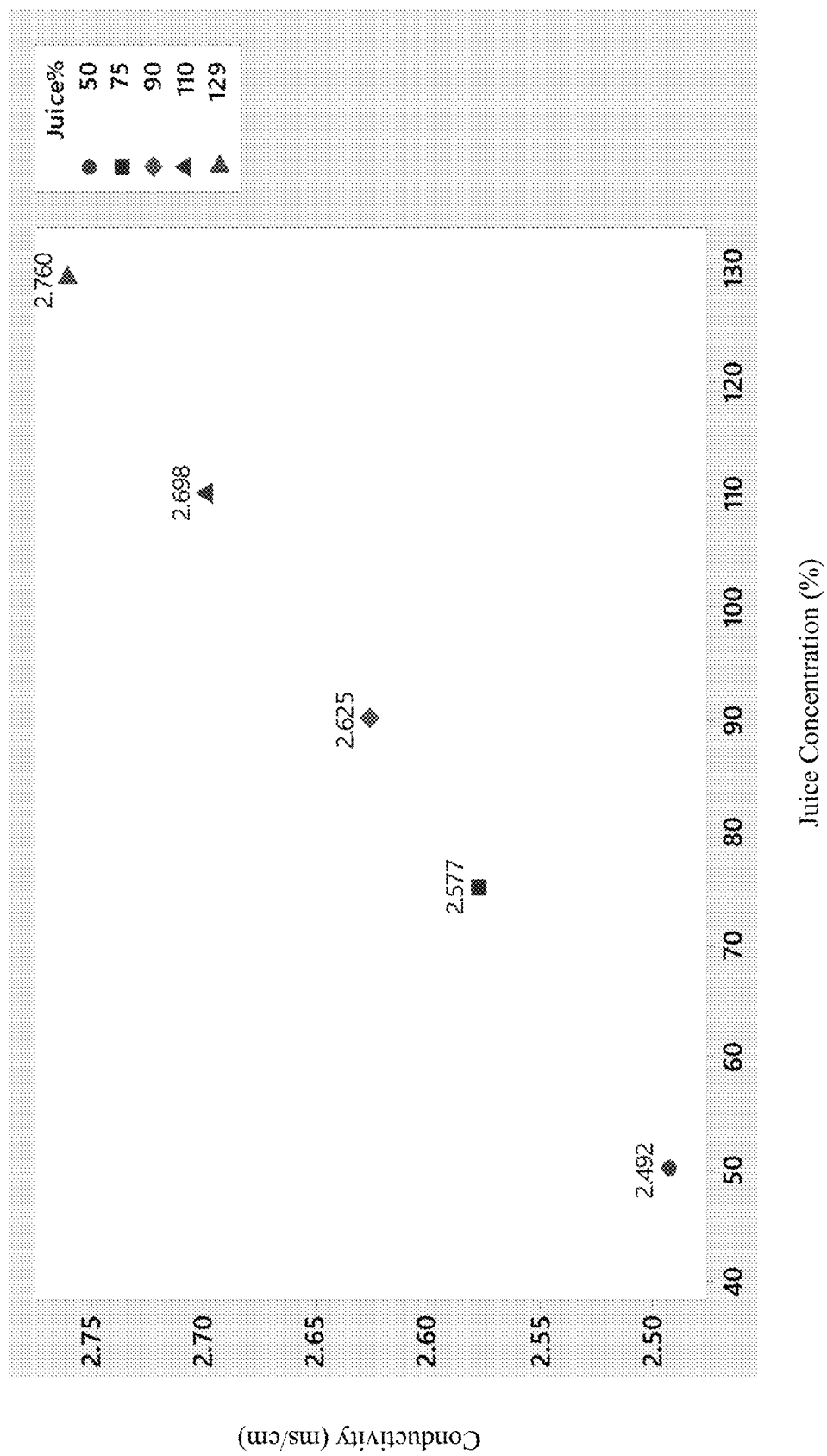
FIG. 7 is a graph of conductivity of the second exemplary syrup as a function of juice level.

The effect of juice concentration on the syrup conductivity was investigated by maintaining the preservative and acid concentrations constant and varying the juice concentration. The measured syrup conductivity as a function of juice concentration is shown in FIG. 7. As can be seen from FIG. 7, the conductivity of the syrup decreases as the juice concentration decreases.

The results in FIGS. 5-7 indicate that if the conductivity of the syrup is decreased, one or more ingredients such as preservative, acid and juice are partially or completely absent in the syrup.

To rule out the possibility that the conductivity decrease is due to the absence of acid and juice, the titratable acidity and pH of syrup #2 samples were measured. Results are given in the following tables.

Titratable acidity and pH values of syrup #2 samples at different potassium benzoate (PB) preservative levels ranging from 0% (i.e., no PB) to 100% (i.e., target PB level) are summarized in Table 4. As can be seen from Table 4, reducing the potassium benzoate preservative content in the syrup results in a decrease in the pH value, however, the titratable acidity remains about the same (i.e., value variation is within the measurement error range and/or the expected production variability).

TABLE 4

Titratable Acidity and pH Values of Syrup #2 Samples at Different Potassium Benzoate (PB) Levels

| | Potassium Benzoate Levels in Syrup (from 0% to 100% of target PB level)) | | | | | | |
|---|---|---|---|---|---|---|---|
| | 0% | 20% | 50% | 75% | 85% | 90% | 100% |
| Titratable Acidity | 0.208 | 0.207 | 0.208 | 0.208 | 0.209 | 0.209 | 0.208 |
| pH | 2.71 | 2.79 | 2.70 | 2.79 | 2.97 | 2.92 | 3.11 |

Titratable acidity and pH values of syrup #2 samples at different acid levels ranging from 75% to 115% of the target acid level are summarized in Table 5. As can be seen from Table 5, reducing the acid content in the syrup results in an increase in the pH value, but a decrease in the titratable acidity.

TABLE 5

Conductivity, Titratable Acidity and pH Values of Syrup #2 Samples at Different Acid Levels

| | Acid Levels in Syrup (from 75% to 1115% of target acid level) | | | | | | |
|---|---|---|---|---|---|---|---|
| | 75% | 85% | 90% | 95% | 105% | 110% | 115% |
| Conductivity [ms/cm] | 2.509 | 2.566 | 2.587 | 2.619 | 2.615 | 2.683 | 2.709 |
| Titratable Acidity | 0.159 | 0.178 | 0.188 | 0.198 | 0.209 | 0.228 | 0.238 |
| pH | 3.11 | 3.06 | 3.05 | 3.04 | 3.02 | 3.01 | 3.00 |

Titratable acidity and pH values of syrup #2 samples at different juice levels ranging from 50% to 129% of, the target juice levels are summarized in Table 6. As can be seen from Table 6, reducing the juice content in the syrup does not affect pH and titratable acidity of the syrup. The pH and titratable acidity remain about the same (i.e., value variation is within the measurement error range and/or the expected production variability).

TABLE 6

Conductivity, Titratable Acidity and pH Values of Syrup #2 Samples at Different Juice Levels

| | Juice Levels in Syrup (from 50% to 129% of target juice level) | | | | |
|---|---|---|---|---|---|
| | 50% | 75% | 90% | 110% | 129% |
| Conductivity [ms/cm] | 2.492 | 2.577 | 2.625 | 2.698 | 2.760 |
| Titratable Acidity | 0.205 | 0.207 | 0.208 | 0.210 | 0.212 |
| pH | 3.02 | 3.04 | 3.04 | 2.92 | 2.99 |

For syrup #2, if the conductivity of the syrup is lower than 2.4 ms/cm which corresponds to the conductivity of a syrup containing at least 80% of preservative, one or more ingredients, e.g., potassium benzoate preservative, critic acid, and/or juice are partially or completely absent in the syrup. In combination with the conductivity measurement, if the titratable acidity is lower than the titratable acidity target value and the pH is above the pH target value, it can be concluded that the syrup contains less acid. If the titratable acidity and pH are not affected, it can be concluded that the syrup contains less juice. If the pH is lower than the target pH value, but the titratable acidity is not affected, it can be concluded that the syrup contains less potassium benzoate preservative because potassium benzoate affects the pH but does not impact titratable acidity of the syrup.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for determining whether a syrup contains a preservative at a needed level, comprising:
    measuring a conductivity of the syrup;
    determining whether the measured conductivity is below a predetermined conductivity value determined based on a target syrup according to a syrup recipe; and
    determining whether the preservative is below the needed level in response to the measured conductivity being below the predetermined conductivity value.

2. The method of claim 1, wherein the predetermined conductivity value corresponds to a conductivity value of a syrup containing the preservative in an amount that is at least 80% of the preservative in the target syrup.

3. The method of claim 1, wherein determining whether the preservative is below the needed level comprises measuring a pH of the syrup.

4. The method of claim 3, wherein determining whether the preservative is below the needed level further comprises determining whether the measured pH is below a predetermined pH value.

5. The method of claim 4, wherein the predetermined pH value corresponds to a pH value of the target syrup.

6. The method of claim 4, wherein determining whether the preservative is below the needed level further comprises measuring a titratable acidity of the syrup.

7. The method of claim 6, wherein determining whether the preservative is below the needed level further comprises determining whether the measured titratable acidity is below a predetermined titratable acidity value.

8. The method of claim 7, wherein the predetermined titratable acidity value corresponds a titratable acidity value of the target syrup.

9. The method of claim 1, wherein the preservative comprises benzoic acid, potassium benzoate, sodium benzoate, calcium benzoate, potassium sorbate, sodium diacetate, sodium propionate, calcium propionate, methyl paraben, natamycin, or sodium nitrate.

10. The method of claim 1, wherein the syrup further comprises an acid and a juice.

11. The method of claim 10, wherein the acid comprises citric acid, malic acid, tartaric acid or lactic acid.

12. The method of claim 10, wherein the juice comprises one or more fruit juices, one or more vegetable juices, or combinations thereof.

13. The method of claim 10, wherein the syrup further comprises a colorant, a sweetener, a vitamin, a mineral, a flavoring agent or combinations thereof.

14. A method for determining whether a syrup contains a preservative at a needed level, comprising:
    measuring a conductivity of the syrup;
    determining a predetermined conductivity value using a target syrup according to a syrup recipe;
    determining whether the measured conductivity is below the predetermined conductivity value;
    measuring a pH of and titratable acidity of the syrup in response to the measured conductivity being below the predetermined conductivity value;
    comparing the measured pH with a predetermined pH value;
    comparing the measured titratable acidity with a predetermined titratable acidity value; and
    determining that the syrup does not contain the preservative at the needed level in response to the pH being below the predetermined pH value and the titratable acidity being comparable to the predetermined titratable acidity value.

15. The method of claim 14, wherein the predetermined conductivity value corresponds to a conductivity value of a syrup containing the preservative in an amount that is at least 80% of the preservative in the target syrup.

16. The method of claim 14, wherein the predetermined pH value corresponds to a pH value of the target syrup.

17. The method of claim 14, wherein the predetermined titratable acidity value corresponds to a titratable acidity value of the target syrup.

18. The method of claim 14, wherein the syrup further comprises an acid and a juice.

19. The method of claim 18, further comprising determining that the syrup contains the acid in an amount below a target amount as set in the syrup recipe in response to the pH being above the predetermined pH value and the titratable acidity being below the predetermined titratable acidity value.

20. The method of claim 18, further comprising determining that the syrup contains the juice in an amount below a target amount as set in a syrup recipe in response to the pH being comparable to the predetermined pH value and the titratable acidity being comparable to the predetermined titratable acidity value.

* * * * *